United States Patent [19]
Valentini et al.

[11] Patent Number: 4,877,029
[45] Date of Patent: Oct. 31, 1989

[54] SEMIPERMEABLE NERVE GUIDANCE CHANNELS

[75] Inventors: Robert F. Valentini; Patrick Aebischer; Pierre M. Galletti, all of Providence, R.I.

[73] Assignee: Brown University Research Foundation, Providence, R.I.

[21] Appl. No.: 32,489

[22] Filed: Mar. 30, 1987

[51] Int. Cl.⁴ .............................................. A61B 17/04
[52] U.S. Cl. .................................... 128/334 R; 623/12
[58] Field of Search ............................. 128/334; 623/12

[56] References Cited

U.S. PATENT DOCUMENTS

| | | | |
|---|---|---|---|
| 3,786,817 | 1/1974 | Palma | 128/334 |
| 3,833,002 | 9/1974 | Palma | 128/334 |
| 3,916,905 | 11/1975 | Kuhn | 128/334 |
| 3,960,152 | 6/1976 | Augurt et al. | 128/335.5 |
| 3,988,411 | 10/1976 | Capozza | 264/184 |
| 4,033,938 | 7/1977 | Augurt et al. | 260/78.3 |
| 4,074,366 | 2/1978 | Capozza | 3/1 |
| 4,481,353 | 11/1984 | Nyilas et al. | 528/303 |
| 4,534,349 | 8/1985 | Barrows | 128/334 |

FOREIGN PATENT DOCUMENTS 0261833 3/1988 European Pat. Off. ........ 128/334 R

OTHER PUBLICATIONS

Midgley et al., *Surgical Forum*, vol. 19, pp 519–520, (1968).
Ducker et al., *Improvements in Silastic Cuffing*, pp. 582–587 (1967).
Molander et al., *Nerve Regeneration Through Polyglactin Tube*, vol. 5, pp. 54–57.
Lundborg et al., *Journal of Neuropathology and Experimental Neurology*, vol. 41, No. 4, pp. 412–422 (1982).
Uzman et al., *Journal of Neuroscience Research*, vol. 9, pp. 325–338 (1983).
Nyilas et al., *Trans AM Soc Artif Intern Organs*, vol. XXIX, pp. 307–313.
Seckel et al., *Plastic & Reconstructive Surgery*, vol. 74, pp. 173–181, (1983).
daSilva et al., *Brain Research*, vol. 342, pp. 307–315 (1985).
De Rossi et al., *ASAIO*, vol. 5, No. 1, pp. 1–11 (1983).
Fukada, *Mechanisms of Growth Control*, pp. 192–210, (1981).

*Primary Examiner*—Edward M. Coven
*Assistant Examiner*—Gary Jackson
*Attorney, Agent, or Firm*—Thomas J. Engellenner; Ann-Louise Kerner

[57] ABSTRACT

Medical devices employing semipermeable materials, such as acrylic copolymers, polyurethane isocyanate, and other biocompatible semipermeable polymers, are disclosed for use as guidance channels in regenerating nerves. The devices can be formed by tubular semipermeable conduits adapted to receive the ends of a severed or damaged nerve. The tubular conduits define lumens through which axons can regenerate to restore motor and/or sensory functions. The guidance materials are chosen such that they are capable of allowing the diffusion of nutrients and other metabolites to the regenerating nerve site while excluding fibroblasts and other scar-forming cells. In particular, tubular channels which have a smooth inner surface and longitudinally oriented trabeculae result in significantly larger regenerated nerve cables and higher numbers of regenerated myelinated axons.

7 Claims, 3 Drawing Sheets

SEMIPERMEABLE NERVE GUIDANCE CHANNELS

BACKGROUND OF THE INVENTION

The technical field of this invention concerns medical devices useful for the repair of injured nerves and methods for preparing and using such devices for nerve repairs.

The problem of repairing severed nerves is a long-standing one that has plagued surgeons for over a hundred years. Despite advances in microsurgical techniques, a patient's recovery from a serious wound is often limited by a degree of nerve damage which cannot be repaired. The replanting of amputated fingers and limbs is especially limited by poor nerve regeneration.

When a nerve is severed, the functions supplied by that nerve, both motor and sensory, are lost. The nerve cells' appendages (axons) in the distal (the furthest away from the spinal cord) portions of the severed nerve degenerate and die leaving only the sheaths in which they were contained. The axons in the proximal stump that are still connected to the spinal cord or dorsal root ganglion, also suffer some degeneration. The degeneration generally does not proceed to the death of the entire nerve cell bodies. If the injury occurs far enough from the nerve cell bodies, regeneration will occur. Axonal sprouts will appear from the tip of the regenerating axon. These sprouts grow distally and attempt to reenter the intact neurilemnal sheaths of the distal portion of the severed nerve. If entry is successfully made, axonal growth will continue down these sheaths and function will eventually be restored.

In the conventional approach to nerve repair, an attempt is made to align the cut ends of the fascicles (nerve bundles within the nerve trunk). A similar approach is taken with smaller nerves. In either case, the chief hazard to the successful repair is the trauma produced by the manipulation of the nerve ends and the subsequent suturing to maintain alignment. The trauma appears to stimulate the growth and/or migration of fibroblasts and other scar-forming connective tissue cells. The scar tissue prevents the regenerating axons in the proximal stump from reaching the distal stump to reestablish a continuous pathway. The result is a permanent loss of sensory or motor function.

Various attempts have been made over the years to find a replacement for direct (i.e., nerve stump-to-nerve-stump suturing). Much of the research in this field has focused on the use of "channels" or tubular prostheses which permit the cut ends of the nerve to be gently drawn into proximity and secured in place without undue trauma. It is also generally believed that such channels can also prevent, or at least retard, the infiltration of scar-forming connective tissue.

The use of silastic cuffs for peripheral nerve repair was reported by Ducker et al. in Vol. 28, *Journal of Neurosurgery*, pp. 582–587 (1968). Silicone rubber sheathing for nerve repair was reported by Midgley et al. in Vol. 19, *Surgical Forum*, pp. 519–528 (1968) and by Lundborg, et al. in Vol. 41, *Journal of Neuropathology in Experimental Neurology*, pp. 412–422 (1982). The use of bioresorbable polyglactin mesh tubing was reported by Molander et al. in Vol. 5, *Muscle & Nerve*, pp. 54–58 (1982). The use of semipermeable acrylic copolymer tubes in nerve regeneration was disclosed by Uzman et al. in Vol. 9, *Journal of Neuroscience Research*, pp. 325–338 (1983). Bioresorbable nerve guidance channels of polyesters and other polymers have been reported by Nyilas et al. in Vol. 29, *Transactions Am. Soc. Artif. Internal Organs*, pp. 307–313 (1983) and in U.S. Pat. No. 4,534,349 issued to Barrows in 1985.

Despite the indentification of various materials which can serve as nerve guidance channels, the results of research to date have revealed significant shortcomings in such prostheses. Some of the materials identified above have lead to inflammatory reactions in the test animals and have failed to exclude scar tissue formation within the channels. Moreover, the total number of axons, the number of myelinated axons, the thickness of the epineurium, and the fascicular organization of nerves regenerated within guidance channels are all typically less than satisfactory and compare poorly with the original nerve structure of the test animals. Moreover, the loss of sensory or motor function is still the most common outcome of such laboratory experiments.

There exists a need for a better materials and methods for formation of nerve guidance channels. Materials and methods for nerve repair that would minimize surgical trauma, prevent interference with nerve growth by scar tissue, and improve the chances for successful recovery of sensory or motor function, would satisfy a long-felt need in this field.

SUMMARY OF THE INVENTION

It has been discovered that the repair of severed or avulsed nerves can be greatly enhanced by the use of selectively permeable polymeric materials as nerve guidance channels. Medical devices employing such selectively permeable materials, particularly semipermeable tubular devices having smooth inner skins, are disclosed for use in regenerating nerves. The devices can be formed from various polymeric materials, such as acrylic copolymers, polyvinylidene fluoride or polyurethane isocyanate, adapted to receive the ends of the severed or otherwise damaged nerve. The tubular membrane defines a lumen through which axons can be regenerated to restore motor and/or sensory functions.

The terms "semipermeable" and "selectively permeable" are used herein to describe materials which are capable of allowing the exchange of nutrients and other metabolites with the regenerating nervous tissue while excluding fibroblasts and other scar-forming cells. Preferably, the materials allow passage therethrough of solutes having a molecular weight of about 100,000 daltons or less.

The nerve guidance channels of the present invention are also preferably designed to retain nerve growth factors secreted at the anastomatic site or seeded therein, as well as retain any luminal matrix material placed inside the guidance channels. The porosity of the membranes can also be selected to create an immune barrier between the anastomatic site and the patient's immune system.

It has also been discovered that particular structural configurations of the guidance channel can play an important role in optimizing nerve regrowth conditions. Semipermeable, tubular channels which have a smooth, inner surface result in significantly larger regenerated nerve cables and higher numbers of regenerated myelinated axons. In one preferred embodiment, the guidance channels of the present invention comprise tubular membranes featuring relatively large (i.e., on the order of about 1 to about 20 microns) pores on the outside, intercommunicating voids in the membrane, itself, and a smooth inner skin having relatively small (i.e., on the order of about 20 to about 200 angstroms) pores.

The relatively large outside pores and the intercommunicating voids permit capillary ingrowth into the wall of the synthetic tube which allows more optimal metabolic support, while the relatively small pores of the inner membrane prevent the invasion of scar-forming cells within the regenerating environment. Additionally, it is preferable to employ devices having membranes with longitudinally oriented trabeculae rather than radially oriented trabeculae. Studies to date reveal that longitudinally oriented trabeculae can support a larger number of capillaries and yield nerve cables with larger numbers of axons.

The semipermeable nerve guidance channels of the present invention can also be biodegradable. Various techniques known in the art, such as the use of biodegradable derivatives or the formation of copolymers having a biodegradable components can be employed to obtain a satisfactory degree of biodegradability in use. If the channel is not totally biodegradable over time, it can be formed with longitudinal lines of weakness to facilitate removal from about the regenerated nerve after healing has progressed sufficiently.

Preferably, the membrane wall thickness of the semipermeable nerve guidance channels of the present invention will range from about 0.05 to about 1.0 millimeters depending upon the particular membrane material and application. Similarly, the diameter of the lumen can vary from about 0.5 millimeters to about 2 centimeters, depending upon the size of nerve to be repaired.

The nerve guidance channels of the present invention are used by locating the severed nerve ends, and selecting an appropriately sized semipermeable tubular device for the repair, having openings adapted to receive the ends of the severed nerve and a lumen to permit regeneration of the nerve therethrough. The cut ends of the nerve are then gently drawn into tube by manual manipulation or suction, placed in optimal proximity and then secured in position without undue trauma by sutures through the tube, or by a biocompatible adhesive (e.g., fibrin glue) or by frictional engagement with the tube. Antibiotics can be administered to the site, and the wound is then closed.

The term "nerve" is used herein to mean both monofascicular and polyfascicular nerves. The same general principals of regeneration with semipermeable nerve guidance channels are applicable to both.

The invention will next be described in connection with certain preferred embodiments; however, it should be clear that various changes, additions and subtractions can be made by those skilled in the art without departing from the spirit or scope of the invention. For example, although the semipermeable nerve guidance channels described below are generally tubular in shape, it should be clear that various alternative shapes can be employed. The lumens of the guidance channels can be oval or even square in cross-section. The guidance channels can also be constructed from two or more parts which are clamped together to secure the nerve stumps. Moreover, semipermeable sheet materials can be employed and formed into a tube in situ. In such a procedure, the nerve stumps can be placed on top of the sheet and secured thereto by sutures, adhesives or friction. The sheet is then wrapped around the nerve segments and the resulting tube is closed by further sutures, adhesives or friction.

Various materials can also be used to fill the luminal cavity. For example, the cavity can be filled with physiological saline, laminin, collagen, glycosaminoglycans, or nerve growth factors. The cavity can also be seeded with cultured Schwann cells.

DETAILED DESCRIPTION

The invention will next be described in connection with the following examples and comparative experiments.

Young female CD-1 mice (25-30 g) (Charles River Lab., Wilmington, MA) were housed in temperature and humidity-controlled rooms and received food and water ad libitum. The mice were anesthetized with methoxyfluorane and the left sciatic nerve was exposed through an incision along the anterior-medial aspect of the upper thigh. After retraction of the gluteus maximus muscle, a 3-4 mm segment of nerve proximal to the tibio-peroneal bifurcation was resected and discarded.

A series of materials were then tested as nerve guidance channels. The materials were all tubular in shape and 6 mm long. The nerve stumps were anchored 4 mm apart within the tubes using 10-0 nylon sutures placed through holes 1 mm from each channel end. For each material, at least six channels were implanted for a period of four and twelve weeks. A further set of control animals underwent nerve resection as described above, and their section sites were closed without implantation of any guidance material. Aseptic surgical technique was maintained throughout the procedures, which were performed with the aid of an operating microscope.

A variety of tubular materials impermeable or indiscriminately permeable to watery solutes were compared to semi-permeable guidance channels. The impermeable materials included polyethylene (Clay Adams, Parsippany, N.J.) and silicone elastomer (SilMed, Taunton, Mass.) and the indiscriminately permeable material was expanded polytetrafluoroethylene (Gore, Flagstaff, Ariz.). The semipermeable channels (Amicon Corp., Lexington, Mass.) were composed of an acrylic copolymer and featured a partially fenestrated outer skin and a permselective inner skin (with a nominal molecular weight cutoff of 50,000 daltons) connected by an open, trabecular structure with longitudinally communicating voids.

At retrieval time, the animals were deeply anesthetized and perfused transcardially with 5 ml of phosphate-buffered saline (PBS) followed by 10 ml of a fixative containing 3.0% paraformaldehyde and 2.5% glutaraldehyde in PBS at pH 7.4. The operative site was reopened and the guidance channel and segments of the native nerve at either channel end were removed. The specimens were then post-fixed in a 1% osmium tetroxide solution, dehydrated and embedded in Spurr resin.

Transverse sections taken at the midpoint of the guidance channel were cut on a Sorvall MT-5000 microtome. The sections (1 micron thick) were stained with toluidine blue. Whole mounts of nerve were displayed on a video monitor through a Zeiss IM35 microscope. Nerve cable cross-sectional area and the number of myelinated axons were determined with the aid of a graphic tablet at a final magnification of 630×. The Wilcoxon rank-sum test was used to assess statistical differences ($p < 0.05$) between the various populations. All values are presented as means ± standard error of the mean.

Figure 1:
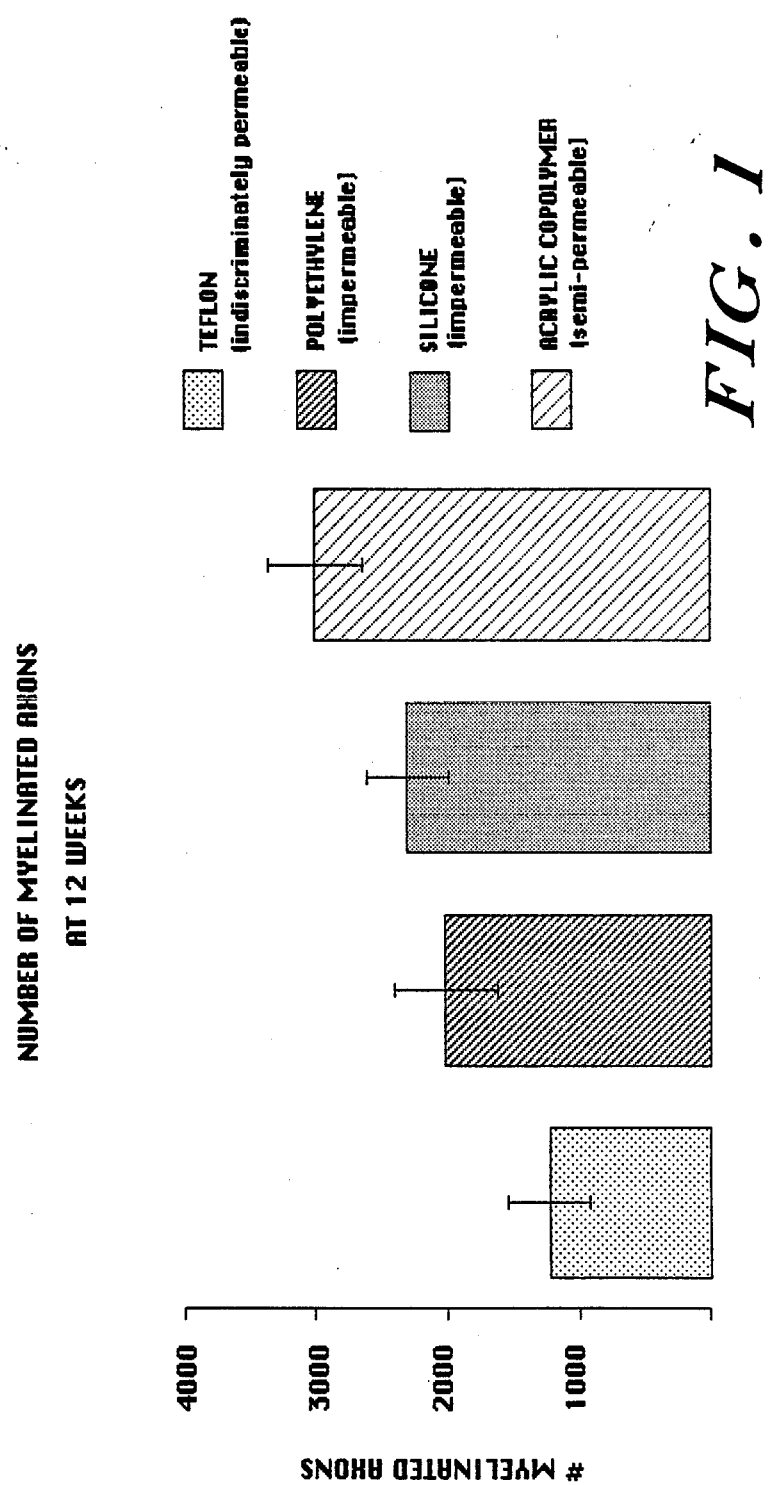
FIG. 1 is a comparative graph of the regenerative capabilities (in terms of numbers of myelinated axons) of semipermeable, indiscriminately permeable and non-permeable nerve guidance materials.
Figure 2:
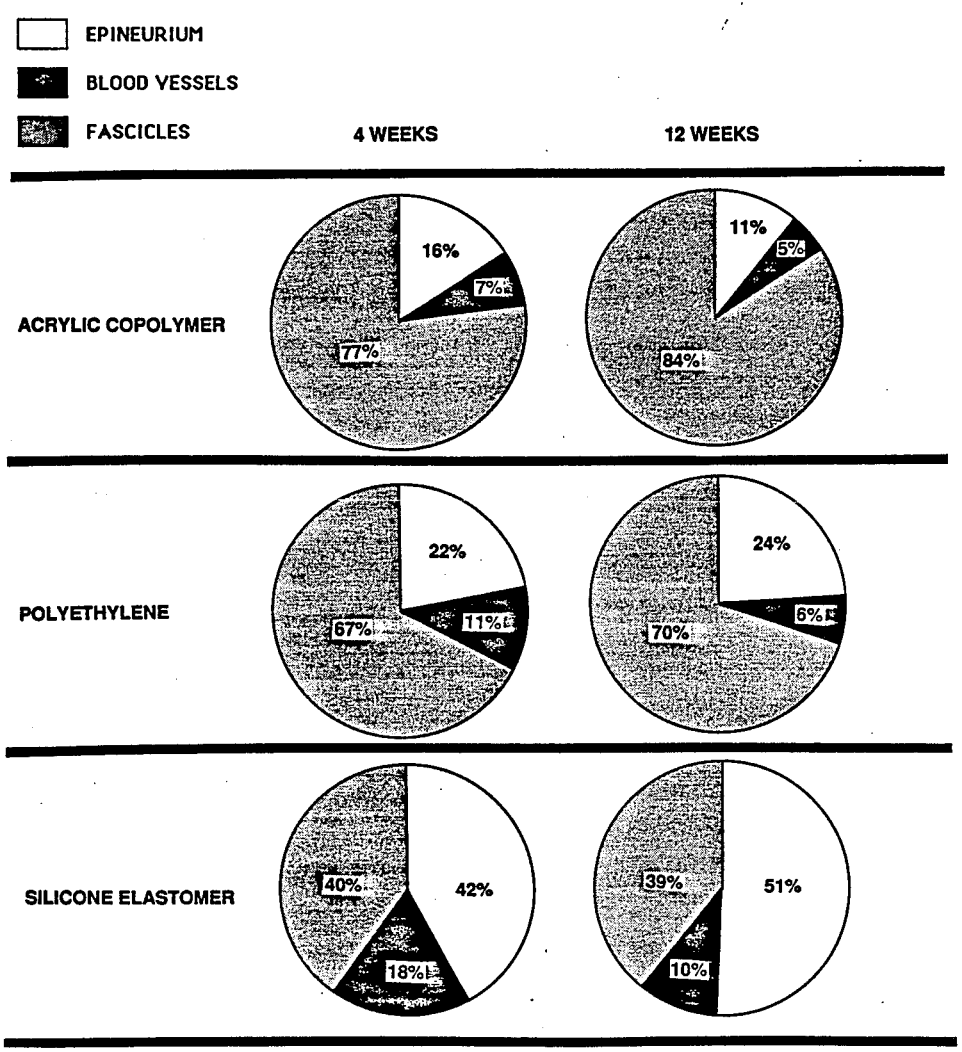
FIG. 2 is a comparative chart of the regenerative capabilities (in terms of relative cross-sectional area of different nerve cable components in percent) for semipermeable and non-permeable nerve guidance materials.

The success rate and quality of peripheral nerve regeneration was dramatically enhanced through the use of a semipermeable material. The semipermeable channels supported the regeneration of a nerve cable 100 percent of the time, while the impermeable materials supported regeneration about 70 percent of the time. Indiscriminately permeable channels supported the regeneration of dispersed tissue which never organized into a true nerve cable. FIGS. 1 and 2 show the morphological results of the comparative studies. FIG. 1 shows the significantly higher number of myelinated axons which regenerated in semipermeable channels. FIG. 2 shows the tissue composition of the regenerated nerves. The nerves regenerated in semipermeable channels always display the greatest area of fascicle tissue and the lowest area of epineurial and vascular tissue and approach the tissue composition of normal mouse sciatic nerve. Nerves which were not repaired with a guidance channel showed complete degeneration at 12 weeks.

Figure 3:
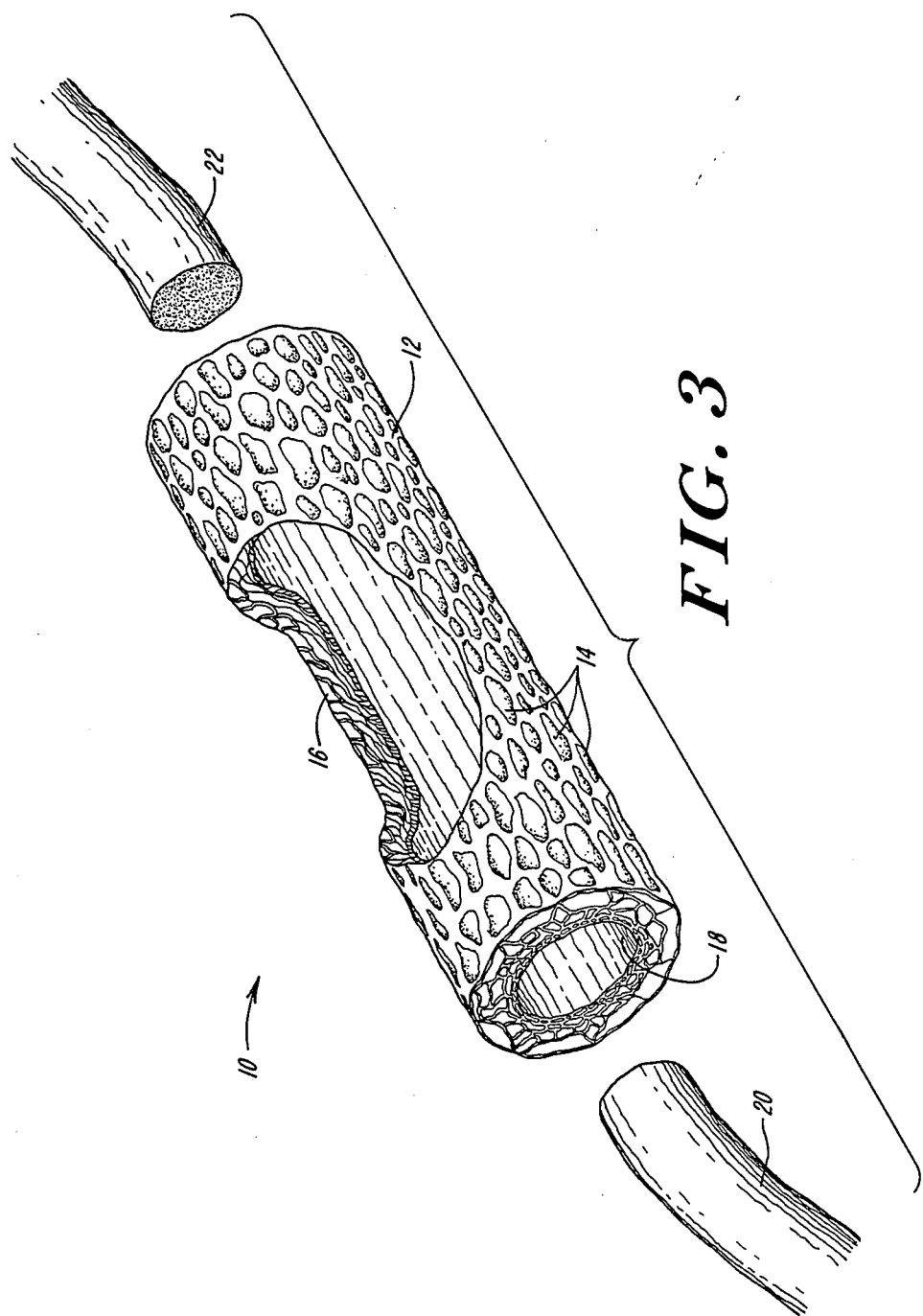
FIG. 3 is a partial cutaway perspective view of a semipermeable nerve guidance channel according to the present invention.

In FIG. 3, the structure of a semipermeable nerve guidance channel 10 is shown including a tubular membrane material 12 having a porous outer surface 14, longitudinally oriented trabeculae 16 and a smooth, semipermeable inner membrane surface 18. In operation, the ends of a severed nerve 20, 22 are secured within the tubular membrane 12 to provide a protective guidance channel for the regeneration of the nerve therethrough.

The permselective channels enhance peripheral nerve regeneration by supporting the formation of a favorable regenerating environment. The permselective characteristics of the inner membrane 18 allow the exchange of nutrients, while concentrating growth factors released by the nerve and excluding scar-forming cells. The capillaries which grow into the open trabeculae 16 through the macroporous outer skin 14 of the tube facilitate the provision of nutrients to and the removal of waste products from the regenerating nerve. These factors result in the consistent regeneration of morphological characteristics as compared to other guidance channels materials. These important nerve characteristics favor the return of motor and sensory function.

We claim:

1. A medical device for use in regenerating a severed nerve, the device comprising a tubular semipermeable membrane having openings adapted to receive the ends of a severed nerve, at least one longitudinally-oriented trabecula within the membrane to provide a passageway for capillary ingrowth, a porous outer membrane surface which permits capillary ingrowth into said trabecula, and a semipermeable inner membrane surface, whereby the tubular membrane device provides a protective guidance channel for the regeneration of said nerve therethrough.

2. The device of claim 1 wherein the thickness of the membrane ranges from about 0.05 to about 1.0 millimeter.

3. The device of claim 1 wherein the lumen has a diameter ranging from about 0.5 millimeters to about 2 centimeters.

4. the device of claim 1 wherein the membrane is permeable to solutes having a molecular weight of about 100,000 daltons or less.

5. The device of claim 1 wherein the inner membrane surface is impermeable to fibroblasts and other scar-forming connective tissue cells.

6. The device of claim 1 wherein the outer membrane surface has pores which range in size from about 1 to about 20 microns.

7. The device of claim 1 wherein the inner membrane surface has pores which range in size from about 20 to about 200 angstroms.

* * * * *